| United States Patent [19] | [11] Patent Number: 5,068,450 |
| Crochemore et al. | [45] Date of Patent: Nov. 26, 1991 |

[54] PROCESS FOR THE PREPARATION OF AROMATIC ALDEHYDES

[75] Inventors: Michel Crochemore, Chaponost; Christophe Rochin, Lyons, both of France

[73] Assignee: Rhone-Poulenc Chimie, Courbevoie Cedex, France

[21] Appl. No.: 490,495

[22] Filed: Feb. 28, 1990

Related U.S. Application Data

[63] Continuation of Ser. No. 217,699, Jul. 11, 1988, abandoned.

[30] Foreign Application Priority Data

Jul. 10, 1987 [FR] France .................................. 87 10180

[51] Int. Cl.$^5$ ............................................. C07C 45/00
[52] U.S. Cl. ...................................................... 568/435
[58] Field of Search ......................................... 568/435

[56] References Cited

U.S. PATENT DOCUMENTS 3,720,718  3/1973  Fenton ................................. 568/435
4,460,794  7/1984  Fujiyama et al. .................... 568/428

Primary Examiner—Bruce Gray
Attorney, Agent, or Firm—Finnegan, Henderson, Farabow, Garrett, and Dunner

[57] ABSTRACT

A process for the preparation of aromatic aldehydes by formylation of aromatic compounds in liquid hydrofluoric acid in the presence of boron trifluoride.

10 Claims, No Drawings

PROCESS FOR THE PREPARATION OF AROMATIC ALDEHYDES

This application is a continuation, of application Ser. No. 07/217,699 filed July 11, 1988 now abandoned.

The present invention relates to a process for the preparation of aromatic aldehydes and, more particularly, to a formylation process.

It is known to prepare aromatic aldehydes according to at least two types of methods:
- a direct method which consists of attaching a CHO group onto an aromatic derivative, and
- an indirect method which consists of oxidizing a group which is already present on the aromatic derivative.

A direct formylation method is disclosed by U.S. Pat. No. 4,588,844, which describes a reaction between an aromatic derivative and urotropine in a hydrofluoric acid medium. This process employs a costly starting material, urotropine, which contains four potential formaldehyde groups, only one of which can be employed to form benzaldehyde. In addition, urotropine must always be employed in a molar quantity relative to the initial aromatic. Also, the yields obtained with compounds such as fluorobenzene are too low to be suitable for industrial utilization.

U.S. Pat. No. 4,622,429 describes a process which consists of reacting an aromatic derivative with carbon monoxide in a superacid medium or in the presence of a Lewis acid. This patent, however, discloses only aromatic derivatives substituted with alkyl, cycloalkyl or benzyl groups as starting materials.

Swiss Pat. No. 597,149 discloses a process consisting of reacting a formamide with an aromatic derivative in the presence of phosphorus oxychloride, phosgene or thiophosgene. This reaction requires the use of considerable safety constraints, which has made the chemical industry reluctant to employ this process.

German Patent No. 2,732,227 discloses a process which consists of reacting a non-aminated aromatic derivative with hydrocyanic acid in an acidic medium and then performing an acid hydrolysis. The use of hydrocyanic acid imposes safety constraints similar to those required by the Swiss patent process.

Documents describing the second known method of preparing aromatic aldehydes include British Patent No. 2,165,536, which discloses the oxidation of derivatives methylated on the aromatic nucleus and Japanese Patent No. 79/66,639, which discloses the oxidation of aromatic derivatives of glyoxalic acid.

These two-stage processes have never been fully satisfactory to industry, because a change of reactor is required which is detrimental to the profitability of the process.

None of the above direct or indirect formylation processes makes it possible to obtain an aromatic aldehyde at an advantageous cost, without the use of severe safety precautions.

The present invention has achieved this objective by providing a process for the preparation of aromatic aldehydes, in which an aromatic compound is reacted with alkyl formate in hydrofluoric acid in the presence of boron trifluoride for a time sufficient to form the aromatic aldehyde.

As used herein, aromatic compound means any monocyclic, polycyclic, homocyclic or heterocyclic aromatic compound substituted by one or more elements selected from among hydrogen and the halogens, preferably fluorine, or alkyl, alkoxy, hydroxyl, perhaloalkoxy, thioalkyl, phenoxy and phenyl groups.

The aromatic compounds are preferably represented by the following formula (I)

$$(R)_n-Ar$$

in which:
Ar is selected from a monocyclic, polycyclic, homocyclic or heterocyclic radical,
  n is an integer ranging from 1 to 3, and
  R is selected from alkyl groups containing 1 to 6 carbon atoms, alkoxy groups containing 1 to 6 carbon atoms, perhaloalkoxy or thioalkyl groups containing 1 to 6 carbon atoms, halo, preferably fluoro, and phenoxy or optionally substituted phenyl groups.

Preferred starting materials which may be employed in the process of the present invention include benzene, fluorobenzene, chlorobenzene, phenyl ether, guaiacol, anisole and biphenyl.

Methyl, ethyl, n-propyl and n-butyl formates are among the preferred alkyl formates which can be utilized in the process of the invention.

The hydrofluoric acid employed is preferably anhydrous. The use of aqueous hydrofluoric acid is permissible but would result in a useless consumption of boron trifluoride in the form of $HF.BF_3.H_2O(H_3O^+BF_4^-)$.

Preferably, a quantity of hydrofluoric acid is employed such that the molar ratio of hydrofluoric acid to the aromatic compound ranges from 5:1 to 50:1.

Preferably, a quantity of alkyl formate is utilized such that the molar ratio of the alkyl formate to the aromatic compound ranges from reaction stoichiometry to 2, and more preferably ranges from 1:1 to 1.5:1.

It is preferable to employ a quantity of boron trifluoride such that the absolute pressure of $BF_3$ in the reaction space ranges from 1 to 20 bars. A pressure of greater than 20 bars may be utilized but offers no particular advantages.

The process of the invention is preferably carried out at a temperature ranging from 0° to 100° C.

The reaction time varies with the starting materials employed and with the reaction temperature. A period of a few hours appears to suit many of the starting materials when a temperature between 30° and 60° C is employed.

The product resulting from the reaction is easily isolated either by distillation of the hydrofluoric acid or by extraction with any solvent known to one of ordinary skill in the art, such as methylene chloride, isopropyl ether, methyl isobutyl ketone or toluene.

Benzaldehyde, fluorobenzaldehyde, chlorobenzaldehyde, phenoxybenzaldehyde, 3-methoxy-4-hydroxybenzaldehyde, 4-methoxybenzaldehyde, 2-methoxybenzaldehyde and ° phenylbenzaldehyde are among the preferred compounds which may be obtained by the present process.

The examples which follow are given by way of guidance and should not in any way be considered as limiting the invention.

Example 1 relates to the formylation of fluorobenzene with methyl formate in an $HF:BF_3$ medium.

EXAMPLE 1

A solution of fluorobenzene (0.025 mole, 2.4 g) in methyl formate (0.033 mole, 2 g) was introduced at $-5°$ C. into 20 g of anhydrous HF. The mixture was pressurized to 10 bars with BF$_3$ and was then heated to 60° C. for 6 hours.

After cooling to 0° C, the reaction mixture was drained onto 80 g of ice, extracted with 100 ml of isopropyl ether and neutralized with a saturated solution of potassium bicarbonate.

The organic phase was separated off and dried over KF.

The yields were determined by gas phase chromatography.

A number of aromatic substrates were subjected to this formylation reaction with methyl formate (HCOOMe) in the following ratio: 0.025 mole of substrate per 0.033 mole of methyl formate. Table 1 describes the conditions employed and illustrates the following results obtained:
  degree of conversion of the substrate (DC),
  the particular aldehyde formed,
  selectivity for each aldehyde, and
  the conversion yield (CY).

EXAMPLE 2

Example 1 was reproduced using fluorobenzene but replacing methyl formate by ethyl formate.

After 6 hours reaction at 60° C., 85% yield of para-fluorobenzaldehyde was obtained.

We claim:

1. A process for the preparation of an aromatic aldehyde comprising the step of contacting an aromatic compound substituted by at least one substituent selected from hydrogen, halogen, alkyl, alkoxy, hydroxyl, perhaloalkoxy, thioalkyl, phenoxy and phenyl with an alkyl formate in liquid hydrofluoric acid and in the presence of boron trifluoride for a time sufficient to form said aromatic aldehyde.

2. The process of claim 1, wherein said aromatic compound has the formula (I)

$$(R)_n - Ar$$

TABLE I

| Substrates | BF$_3$ pressure (bar) | T (°C.) | t (hours) | DC (%) | Products | CY (%) |
|---|---|---|---|---|---|---|
| ⌬—F | 10 | 60 | 6 | 95 | F—⌬—CHO | 85 |
|  | 2.5 | 40 | 4 | 55 |  | 92 |
| ⌬—O—⌬ | 5 | 50 | 5 | 80 | ⌬—O—⌬—CHO | 63 |
|  | 10 | 50 | 5 | 85 |  | 63 |
|  | 10 | 30 | 5 | 20 |  | 63 |
| HO—⌬(OMe) | 5 | 50 | 5 | 90 | HO—⌬(OMe)—CHO | 45 |
| MeO—⌬ | 10 | 50 | 4 | 25 | 45% OMe—⌬—CHO (ortho); 55% MeO—⌬—CHO (para) | 95 |
|  | 5 | 50 | 5 | 25 | 58% CHO—⌬—OMe (ortho); 42% MeO—⌬—CHO (para) | 95 |
| ⌬—⌬ | 10 | 60 | 6 | 55 | ⌬—⌬—CHO | 95 |

(I)

wherein: Ar is an aromatic compound;

n is an integer ranging from 1 to 3; and

R is selected from alkyl groups containing 1 to 6 carbon atoms, alkoxy groups containing 1 to 6 carbon atoms, perhaloalkoxy groups containing 1 to 6 carbon atoms, thioalkyl groups containing 1 to 6 carbon atoms, halo groups, phenoxy groups and optionally substituted phenyl groups.

3. The process as claimed in claim 2, wherein the compound of formula I is selected from fluorobenzene, diphenyl ether and biphenyl.

4. The process as claimed in claim 2, wherein said alkyl formate is methyl formate.

5. The process as claimed in claim 2, wherein the molar ratio of hydrofluoric acid to the aromatic compound ranges from 1 to 50:1.

6. The process as claimed in claim 2, wherein the molar ratio of the alkyl formate to the aromatic compound ranges from 1 to 1.5:1.

7. The process as claimed in claim 2, wherein the boron trifluoride pressure ranges from 1 to 20 bars.

8. The process as claimed in claim 2, wherein the reaction temperature ranges from 0° to 100° C.

9. The process as claimed in claim 8, wherein the reaction temperature ranges from 30° to 60° C.

10. The process as claimed in claim 2, wherein said liquid hydrofluoric acid is anhydrous.

* * * * *